(12) United States Patent
Birtwistle et al.

(10) Patent No.: US 6,355,234 B1
(45) Date of Patent: *Mar. 12, 2002

(54) SHAMPOO COMPOSITIONS AND METHOD

(75) Inventors: David Howard Birtwistle, Klongtoey; Siripom Dechsinga, Dusit, both of (TH); Andrew Malcolm Murray, South Wirral (GB)

(73) Assignee: Helene Curtis, Inc., Chicago, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/385,281

(22) Filed: Aug. 30, 1999

Related U.S. Application Data

(62) Division of application No. 08/905,582, filed on Aug. 4, 1997, now Pat. No. 5,977,038.

(30) Foreign Application Priority Data

Aug. 5, 1996 (GB) .............................. 9616411

(51) Int. Cl.⁷ .............................. A61K 7/06; A61K 7/08; A61K 7/075
(52) U.S. Cl. ................ 424/70.27; 424/70.1; 424/70.11; 424/70.12; 424/70.19; 424/70.21; 424/70.27; 424/70.31; 510/119; 510/122
(58) Field of Search .............................. 424/70.1, 70.11, 424/70.12, 70.19, 70.21, 70.22, 70.27, 70.31; 510/119, 122, 129

(56) References Cited

U.S. PATENT DOCUMENTS

| | | | |
|---|---|---|---|
| 3,294,725 A | | 12/1966 | Findlay et al. |
| 3,958,581 A | | 5/1976 | Abegg et al. |
| 3,962,418 A | | 6/1976 | Birkofer |
| 4,009,256 A | | 2/1977 | Nowak, Jr. et al. |
| 4,152,416 A | | 5/1979 | Spitzer et al. |
| 5,085,857 A | | 2/1992 | Reid et al. |
| 5,720,964 A | * | 2/1998 | Murray ........................ 424/401 |

FOREIGN PATENT DOCUMENTS

| | | |
|---|---|---|
| EP | 0529883 | 3/1993 |
| WO | 92/10162 | 6/1992 |
| WO | 95/22311 | 8/1995 |

* cited by examiner

*Primary Examiner*—Thurman K. Page
*Assistant Examiner*—Brian K. Seidleck
(74) *Attorney, Agent, or Firm*—Matthew Boxer

(57) ABSTRACT

An aqueous conditioning shampoo composition comprising, in addition to water:

i) at least one surfactant chosen from anionic, nonionic, zwitterionic or amphoteric surfactants or mixtures thereof:

ii) emulsified particles of an insoluble, nonvolatile silicone;

iii) a soluble cationic hair conditioning polymer having a cationic charge density of about +3.0 meq/gram or less, in which the emulsified particles of insoluble, nonvolatile silicone are incorporated into the shampoo composition as a preformed aqueous emulsion having an average silicone particle size in the emulsion and in the shampoo composition of from 2 to 30 microns.

12 Claims, No Drawings

SHAMPOO COMPOSITIONS AND METHOD

This is a divisional of Ser. No. 08/905,582, filed Aug. 4, 1997, now U.S. Pat. No. 5,977,038.

FIELD OF THE INVENTION

This invention relates to shampoo compositions, and more particularly to shampoo compositions containing emulsified particles of silicone, which compositions condition the hair leaving it softer and more manageable.

BACKGROUND OF THE INVENTION

The use of silicones as conditioning agents in cosmetic formulations is well known and widely documented in the patent literature. Generally, dispersed droplets of the silicone oil are suspended in the composition, which is then applied to the hair to deposit the silicone material on the hair shaft.

A typical method of silicone shampoo manufacture is disclosed in WO 92/10162. Essentially, the silicone material is emulsified directly into the shampoo by an in situ hot process, in which the complete shampoo mixture incorporating the silicone is mixed thoroughly at elevated temperature, pumped through a high shear mill and then cooled. The silicone can be dispersed in a first process stage with anionic surfactant and fatty alcohol to form a premix. The premix is then mixed with the remaining materials of the shampoo, pumped through a high shear mill, and cooled to obtain the final composition.

A disadvantage associated with an in situ hot process such as is described in WO 92/10162 is that factory handling of viscous silicone oil is difficult in the context of a full shampoo manufacturing operation.

A further disadvantage is that special equipment is normally needed to control silicone particle size during manufacture. GB 2 170 216 A discloses a similar process, in which the full shampoo composition incorporating insoluble, non-volatile silicone is sheared with a high shear mixer until the silicone particles are on average less than 2 microns in diameter. The particle size distribution is then said to be from about 2 to about 55 microns.

In order to solve the above mentioned problems with in situ hot processing of silicone, the alternative of incorporating the silicone as a preformed aqueous emulsion has been proposed. Such a method has the consequences that the silicone is incorporated with a predeterminable, controllable particle size distribution. The silicone is insoluble and remains emulsified in the fully formulated shampoo composition, and thus the step of high shear processing of the silicone within the fully formulated shampoo composition is not required. This also makes manufacture of the compositions easier.

A typical method for incorporating insoluble, non-volatile silicone materials into a conditioning shampoo is disclosed in U.S. Pat. No. 5,085,857 in which such materials are incorporated in the shampoo composition as a pre-formed aqueous emulsion of average particle size less than 2 microns. All the ingredients are mixed in a simple hot or cold process in which the average particle size of the silicone material in the emulsion remains the same in the final shampoo composition. Preferably, this size is from 0.01 to 1 micron, e.g. 0.4 micron.

EP 0 529 883 A1 discloses hair shampoo compositions made by an equivalent method and comprising microemulsified particles of silicone having a particle size of 0.15 microns or less, e.g., 0.036 microns. Reducing the silicone particle size still further in this way is said to improve stability, optical properties and conditioning performance.

The shampoos of U.S. Pat. No. 5,085,087 and EP 0 529 883 A1 require the presence of a cationic polymer to deposit the silicone efficiently from the formulation onto the hair. A problem encountered with these small particle size silicone/cationic polymer formulations is that they can give an undesirable sensory feel, typically manifest as a perception of "slippiness" and/or heaviness on dry hair.

We have now found that the utilisation of insoluble, non-volatile silicone, in the form of an aqueous, preformed emulsion of large particle size in a surfactant-based shampoo composition will impart conditioning benefit to the hair without the dry hair sensory negatives associated with the prior art compositions discussed above.

Surprisingly and advantageously, we have found that in compositions of our invention, the presence of cationic polymer selectively enhances the wet properties of the shampoo, e.g., wet feel and ease of wet comb—whilst reducing the ease of dry combing. In contrast, we found that the presence of cationic polymer in prior art formulations incorporating cationic polymer and smaller particle size pre-formed silicone emulsions did not give a selective increase in ease of wet combing. Ease of dry combing was increased to at least the same extent.

The selective enhancement of wet properties such as ease of wet combing observed with compositions of the present invention is of benefit to the consumer. This is because consumers need to detangle their hair easily when wet, but when it is dry, if the hair slips through the comb too easily then it can be difficult to put into style.

SUMMARY OF THE INVENTION

The invention provides an aqueous shampoo composition comprising, in addition to water:
   i) at least one surfactant chosen from anionic, nonionic, zwitterionic or amphoteric surfactants or mixtures thereof;
   ii) emulsified particles of an insoluble, nonvolatile silicone;
   iii) a cationic hair conditioning polymer having a cationic charge density of about +3.0 meq/gram or less,
in which the emulsified particles of insoluble, non-volatile silicone are incorporated into the shampoo composition as a preformed aqueous emulsion having an average silicone particle size in the emulsion and in the shampoo composition of from 2 to 30 microns.

In another aspect, the invention provides a method of making such a shampoo composition, by mixing together water, the surfactant, the cationic conditioning polymer and a preformed aqueous emulsion of the silicone, wherein the silicone in the emulsion and in the shampoo composition has an average particle size of from 2 to 30 microns.

DETAILED DESCRIPTION OF THE INVENTION i) Surfactant

The composition according to the invention comprises a surfactant chosen from anionic, nonionic, zwitterionic or amphoteric surfactants or mixtures thereof.

Suitable anionic surfactants include the alkyl sulphates, alkyl ether sulphates, alkaryl sulphonates, alkanoyl isethionates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium ammonium and mono-, di- and triethanolamine salts. The alkyl and acyl groups generally contain from 8 to 18 carbon atoms and may be unsaturated. The alkyl ether sulphates, alkyl ether phosphates and alkyl ether carboxylates may contain from one to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, sodium cocoyl isethionate, sodium lauroyl isethionate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

Nonionic surfactants suitable for use in compositions of the invention may include condensation products of aliphatic ($C_8$–$C_{18}$) primary or secondary linear or branched chain alcohols or phenols with alkylene oxides, usually ethylene oxide and generally having from 6 to 30 ethylene oxide groups. Other suitable nonionics include mono- or di-alkyl alkanolamides. Example include coco mono- or di-ethanolamide and coco mono-isopropanolamide.

Amphoteric and zwitterionic surfactants suitable for use in compositions of the invention may include alkyl amine oxides, alkyl betaines, alkyl amidopropyl betaines, alkyl sulphobetaines (sultaines), alkyl glycinates, alkyl carboxyglycinates, alkyl amphopropionates, alkylamphoglycinates alkyl amidopropyl hydroxysultaines, acyl taurates and acyl glutamates, wherein the alkyl and acyl groups have from 8 to 19 carbon atoms. Examples include lauryl amine oxide, cocodimethyl sulphopropyl betaine and preferably lauryl betaine, cocamidopropyl betaine and sodium cocamchopropionate.

The surfactants are present in shampoo compositions o. the invention in an amount of from 0.1 to 50% by weight, preferably from 0.5 to 30% by weight.

Generally, the surfactants are present in shampoo compositions of the invention in an amount of from 0.1 to 50%, preferably from 5 to 30%, more preferably from 10% to 25% by weight.

ii) Silicone

The shampoo composition of the invention also comprises an insoluble, non-volatile silicone, which may be one or more polyalkyl siloxanes, one or more polyalkylaryl siloxanes, or mixtures thereof. The silicone is insoluble in the aqueous matrix of the composition and so is present in an emulsified form, with the silicone present as dispersed particles.

Suitable polyalkyl siloxanes include polydimethyl siloxanes which have the CAFTAN designation dimethicone, having a viscosity of from 5 to 100,000 centistokes at 25° C. These siloxanes are available commercially from the General Electric Company as the Viscasil series and from Dow Corning as the DC 200 series. The viscosity can be measured by means of a glass capillary viscometer as set out further in Doe Corning Corporate Test Method CTM004 Jul. 20, 1970.

Also suitable is polydiethyl siloxane.

The polyalkylaryl siloxanes which may be used in the compositions of the invention include polymethylphenyl polysiloxanes having a viscosity of from 15 to 65 centistokes at 25° C. The siloxanes are available commercially from the General Electric Company as SF1075 methyl phenyl fluid or from Dow Corning as 556 Cosmetic Grade Fluid.

Also suitable are silicone gums, such as those described in U.S. Pat. No. 4,152,416 (Spitzer), and on General Electric Silicone Rubber product Data Sheet SE 30, SE 33, SE 54 and SE 76. "Silicone gums" denotes polydiorganosiloxanes having a molecular weight of from 200,000 to 1,000,000 and specific examples include polydimethyl siloxane polymers, polydimethyl siloxane/diphenyl/methylvinylsiloxane copolymers, polydimethylsiloxane/methylvinylsiloxane copolymers and mixtures thereof.

Aminofunctional silicones which have the CTFA designation amodimethicone, are also suitable for use in the compositions of the invention, as are polydimethyl siloxanes having hydroxyl end groups (which have the CTFA designation dimethiconol).

The silicone materials described above are incorporated in the shampoo composition of the invention as a pre-formed aqueous emulsion. The average particle size of the silicone material in this emulsion and in the shampoo composition is from 2 to 30 microns, preferably from 2 to 20 microns, more preferably 3 to 10 microns. Particle size may be measured by means of a laser light scattering technique, using a 2600D Particle Sizer from Malvern Instruments.

The pre-formed emulsion may be prepared by high shear mechanical mixing of the silicone and water, or by emulsifying the insoluble, non-volatile silicone with water and an emulsifier—mixing the silicone into a heated solution of the emulsifier for instance, or by a combination of mechanical and chemical emulsification. A further suitable technique for preparation of the emulsions is emulsion polymerisation. Emulsion polymerised silicones as such are described in U.S. Pat. No. 2,891,920 (Hyde), U.S. Pat. No. 3,294,725 (Findlay) and U.S. Pat. No. 3,360,491 (Axon).

Any surfactant materials either alone or in admixture may be used as emulsifiers in the preparation of the pre-formed silicone emulsions. Suitable emulsifiers include anionic, cationic and nonionic emulsifiers. Examples of anionic emulsifiers are alkylarylsulphonates, e.g., sodium dodecylbenzene sulphonate, alkyl sulphates e.g., sodium, lauryl sulphate, alkyl ether sulphates, e.g., sodium lauryl ether sulphate nEO, where n is from 1 to 20 alkylphenol ether sulphates, e.g., octylphenol ether sulphate nEO where n is from 1 to 20, and sulphosuccinates, e.g., sodium dioctylsulphosuccinate.

Examples of nonionic emulsifiers are alkylphenol ethoxylates, e.g., nonylphenol ethoxylate nEO, where n is from 1 to 50, alcohol ethoxylates, e.g., lauryl alcohol nEO, where n is from 1 to 50, ester ethoxylates, e.g., polyoxyethylene monostearate where the number of oxyethylene units is from 1 to 30.

Typically, a pre-formed emulsion will contain around 50% of silicone. Pre-formed emulsions are available from suppliers of silicone oils such as Dow Corning, General Electric, Union Carbide, Wacker Chemie, Shin Etsu, Toshiba, Toyo Beauty Co, and Toray Silicone Co. Examples are the material sold as DC-1310 by Dow Corning, and the materials sold as X-52-1086, X-52-2127 and X-52-2112 by Shin-Etsu.

The compositions of the invention typically contain from 0.01 to 20% by weight, preferably from 0.1 to 10%, more preferably from 0.25 to 3% by weight of insoluble, non-volatile silicone. If less than 0.01% by weight is present in the composition, little conditioning benefit is observed, and if more than 20% by weight is present, the hair will appear greasy.

The aqueous pre-formed emulsion may be incorporated into the shampoo composition in an amount of from 0.02 to 40% by weight, preferably from 0.2 to 20% by weight.

The exact quantity of emulsion will of course depend on the concentration of the emulsion, and should be selected to give the desired quantity of insoluble, non-volatile silicone, in the final composition.

iii) Cationic Conditioning Polymer

A further component of hair treatment compositions of the invention is a cationic conditioning polymer.

The polymer may be a homopolymer or be formed from two or more types of monomers. The molecular weight of the polymer will generally be between 5,000 and 10,000,000, typically at least 10,000 and preferably in the range 100,000 to about 2,000,000. The polymers will have cationic nitrogen containing groups such as quaternary ammonium or protonated amino groups, or a mixture thereof.

The cationic charge density is suitably at least 0.1 meq/g, preferably above 0.8 or higher. The cationic charge density should not exceed 3 meq/g. It is preferably less than 2 meq/g. The charge density can be measured using the Kjeldahl method and should be within the above limits at the desired pH of use, which will in general be from about 3 to 9 and preferably between 4 and 8.

The cationic nitrogen-containing group will generally be present as a substituent on a fraction of the total monomer units of the cationic conditioning polymer. Thus when the polymer is not a homopolymer it can contain spacer non-cationic monomer units. Such polymers are described in the CTFA Cosmetic Ingredient Directory, 3rd edition.

Suitable cationic conditioning polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the composition. In general secondary and tertiary amines, especially tertiary, are preferred.

Amine substituted vinyl monomers and amines can be poly-merized in the amine form and then converted to ammonium by cuaternization.

Suitable cationic amino and quaternary ammonium monomers include, for example, vinyl compounds substituted with dialkyl amincalkyl acrylate, dialkylamino alkylmethacrylate, monoalkylaminoalkyl acrylate, monoalkylaminoalkyl methacrylate, trialkyl methacryloxy-alkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these monomers are preferably lower alkyls such as the $C_1$–$C_3$ alkyls, more preferably $C_1$ and $C_2$ alkyls.

Suitable amine-substituted vinyl monomers include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic conditioning polymers can comprise mixtures of monomer units derived from amine- and/or quaternary ammonium-substituted monomer and/or compatible spacer monomers.

Suitable cationic conditioning polymers include, for example: copolymers of 1-vinyl-2-pyrrolidine and 1-vinyl-3-methyl-imidazolium salt (e.g., Chloride salt) (referred to in the industry by the Cosmetic, Toiletry, and Fragrance Association, "CTFA". as Polyquaternium-16) such as those commercially available from BASF Tyandotte Corn. (Parsippany, N.J., USA) under the LUVIQUAt tradename (e.g., LUVIQUAT FC 370); copolymers of 1-vinyl-2-pyrrolidine and dimethylaminoethyl methacrylate (referred to in the industry by CTFA as Polyquaternium-11) such as those commercially from Gar Corporation (Wayne, N.J., USA) under the GAFQUAT tradename (e.g., GAFQUAT 755N); cationic diallyl quaternary ammonium-containing polymer including, for example, dimethyldiallyammonium chloride homopolymer and copolymers of acrylamide and dimethyldiallyammonium chloride, referred to in the industry (CTFA) as Polyquaternium 6 and Polyquaternium 7, respectively; mineral acid salts of amino-alkyl esters of homo-and co-polymers of unsaturated carboxylic acids having from 3 to 5 carbon atoms, as described in U.S. Pat. No. 4,009,256; and cationic polyacrylamides as described in our copending UK Application No. 9403156.4 (WO95/22311)

Other cationic conditioning polymers that can be used include polysaccharide polymers, such as cationic cellulose derivatives and cationic starch derivatives.

Cationic polysaccharide polymer materials suitable for use in compositions of the invention include those of the formula:

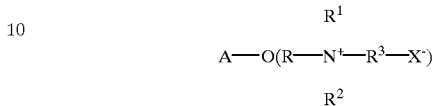

wherein: A is an anhydroglucose residual group, such as starch or cellulose anhydroglucose residual, R is an alkylene axyalklene, polyoxyalkylene, or hydroxyalkylene group, or combination thereof, $R^1$, $R^2$ and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion , as previously described.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10 Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other cationic conditioning polymers that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g., as described in U.S. Pat. No. 3,962,418), and copolymers of etherified cellulose and starch (e.g., as described in U.S. Pat. No. 3,958,581.

Preferably the cationic conditioning polymer is selected from the group comprising cationic polyacrylamides, hydroxyalkyl cellulose ethers and cationic guar derivatives. Particularly preferred are Jaguar C13S with a cationic charge density of 0.8 meq/g. Jaguar C13S is guar hydroxypropyltriamonium chloride. Other particularly suitable materials include Jaguar C15, Jaguar C17 and Jaguar C16 and Jaguar C162, A preferred cellulose ether is Polymer JR400.

As discussed above, we have surprisingly found that in compositions of our invention, inclusion of cationic polymer enhances the wet properties of the shampoo without subsequent dry hair sensory negatives such as slippy feel leading to styling difficulties.

Advantageously, the amount of cationic conditioning polymer present in compositions on the invention is not governed by the requirement that these materials should act as a deposition aid for the silicone component. The particular level appropriate in compositions of the present invention is dependent on the particular surfactant system employed. Generally, the level can vary from 0.01 to 3% by weight.

The invention is also directed to the use, in a shampoo composition comprising a major proportion of a surfactant, of an aqueous pre-formed emulsion of an insoluble, non-volatile silicone having an average particle size in the emulsion and in the shampoo composition of from 2 to 30 microns for imparting improved conditioning benefit to hair from the shampoo composition.

The shampoo composition of the invention may further comprise from 0.1 to 5 % of a silicone suspending agent. Examples are polyacrylic acids, cross linked polymers of acrylic acid, copolymers of acrylic acid with a hydrophobic monomer, copolymers of carboxylic acid- containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and Polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol materials are available from Goodrich and Carbopol is a trade mark.

Suitable cross linked polymers of acrylic acid and acrylate esters are Pemulen TR1 or Pemulen TR2. A suitable heteropolysaccharide gum is xanthan gum, for example that available as Kelzan mu.

Depending on the type of composition employed, one or more additional ingredients conventionally incorporated into hair treatment compositions may be included in compositions of the invention. Such additional ingredients include styling agents, such as resins and hair-setting polymers, perfumes, dyes, buffering or pH adjusting agents, viscosity modifiers, opacifiers, pearlescers, preservatives, antibacterial agents, antidandruff agents, foam boosters, proteins, moisturising agents, herb or other plant extracts and other natural ingredients.

The invention is further illustrated by way of the following non-limitative examples:

EXAMPLES

Shampoo compositions were prepared by mixing the following components in the amounts stated:

Example 1

|  | % wt |
| --- | --- |
| Ammonium lauryl sulphate | 14.0 |
| Cocamidopropyl betaine | 2.0 |
| Silicone Oil[(1)] | 2.0 |
| Carbopol 980[(2)] | 0.4 |
| Jaguar C13S[(3)] | 0.2 |
| Preservative, perfume, viscosity modifier | q.s. |
| Water | to100.0 |

[(1)]Silicone oil was included as DC-1310 from Dow Corning Ltd., an emulsion of dimethicone (60,000 cs) in nonionic surfactant.
[(2)]Carbopol 980 is a cross-linked polyacrylate available from B F Goodrich.
[(3)]Jaguar C13S is guar hydroxypropyltrimonium chloride available from Celanese Corp.

Example 2

|  | % wt |
| --- | --- |
| Ammonium lauryl sulphate | 14.0 |
| Cocamidopropyl betaine | 2.0 |
| Silicone oil[(1)] | 2.0 |
| Carbopol 980 | 0.4 |
| Ethylene glycol monostearate | 1.5 |
| Jaguar C13S | 0.2 |
| Preservative, perfume, viscosity modifier | q.s. |
| Water | to100.0 |

[(1)]as Example 1

Example 3

|  | % wt |
| --- | --- |
| Sodium lauryl ether sulphate 2EO | 12.0 |
| Cocamidopropyl betaine | 4.0 |
| Silicone oil[(1)] | 0.5 |
| Carbopol 980 | 0.4 |
| Jaguar C13S | 0.03 |
| Ethylene glycol monostearate | 1.5 |
| Preservative, perfume, viscosity modifier | q.s. |
| Water | to100.0 |

[(1)]as Example 1

All the shampoos of Examples 1–3 are prepared using a simple cold process whereby all the ingredients are mixed using a paddle stirrer.

The silicone particles in the emulsion have a mean particle size of 7.7 microns and remain the same in the shampoo composition.

Example 4 and Comparative Example A

Evaluation of the wet/dry conditioning performance of shampoo formulations incorporating pre-emulsified silicone of different particle sizes and with or without cationic polymer.

Test Shampoos

Shampoo compositions were prepared containing ingredients as shown in the following Table. Example 4 is a formulation according to the present invention. Comparative Example A is a formulation in which the pre-emulsified large particle size silicone of Example 4 has been substituted by an equivalent amount of a pre-emulsified smaller particle size silicone as described in the prior art. Control 1 is the formulation of Example 4 minus cationic polymer (Jaguar C-13-S). Control 2 is the formulation of Comparative Example A minus cationic polymer (Jaguar C-13-S).

| Ingredient | Example 4 | Control 1 | Comp. Ex. A | Control 2 |
| --- | --- | --- | --- | --- |
| SLES (100%) | 14 | 14 | 14 | 14 |
| CAPB (100%) | 2 | 2 | 2 | 2 |
| Jaguar C-13-S | 0.2 | — | 0.2 | — |

-continued

| Ingredient | Example 4 | Control 1 | Comp. Ex. A | Control 2 |
|---|---|---|---|---|
| DC-1310 (60%) | 3.3 | 3.3 | — | — |
| BY22-026 (50%)[(1)] | — | — | 4 | 4 |
| Carbopol 980 | 0.4 | 0.4 | 0.4 | 0.4 |
| Formalin | 0.1 | 0.1 | 0.1 | 0.1 |
| water | to 100 | to 100 | to 100 | to 100 |

[(1)]BY22-026 is an emulsion of 60,000 cs dimethicone with a particle size of 0.5 microns, ex Toray Silicone Co.

Conditioning Performance

The conditioning performance of each of the above test shampoos was evaluated as follows: 7 g of hair in the form of a switch was worked in 0.7 g of the test product, lathered for 30 seconds, and rinsed with water. The procedure was repeated once. Three switches of hair were prepared for each product to be evaluated. The evaluation of conditioning performance was carried out by twelve trained panellists as a paired comparison test and significant differences at greater than 95% confidence were assessed.

Results

Results are shown in the following table, with each row including entries for two shampoos being compared in the form of relative allocation of a total score of 100, a higher score indicating preference for that member of the pair.

The two attributes assessed by the panellists were (a) ease of wet combing and (b) ease of dry combing.

The results were as follows:

| | Ease of wet comb | Ease of dry comb |
|---|---|---|
| Example 4 versus Control 1 | 70 | 26 |
| Comp. Ex. A versus Control 2 | 72 | 80 |

The results show that:

Example 4 gives significantly greater ease of wet combing than Control 1 on ease of wet combing Control 1 gives significantly greater ease of dry combing than Example 4.

Comparative Example A gives significantly greater ease of wet and dry combing than Control 2.

Conclusions

Example 4 according to the invention shows that inclusion of cationic polymer increases the ease of wet combing imparted by the formulation and reduces the ease of dry combing.

Comparative Example A shows that if the large particle size pre-emulsified silicone of the invention is substituted with a smaller particle size pre-emulsified silicone according to the prior art, then a selective increase in wet combing performance is not observed. In contrast to the Example of the invention, Comparative Example A shows that inclusion of cationic polymer increases the ease of wet combing imparted by the formulation but increases the ease of dry combing (as expressed by panellist preference) to a greater extent.

What is claimed is:

1. An aqueous shampoo composition comprising, in addition to water:
   i) at least one surfactant chosen from anionic, nonionic, zwitterionic or amphoteric surfactants or mixtures thereof;
   ii) emulsified particles of an insoluble, nonvolatile silicone selected from the group consisting of polyalkyl siloxanes, polyalkyl aryl siloxanes, and silicone gums;
   iii) a soluble cationic hair conditioning polymer having a cationic charge density of about +3.0 meq/gram or less, in which the emulsified particles of insoluble, nonvolatile silicone are incorporated into the shampoo composition as a preformed aqueous emulsion having an average silicone particle size in the emulsion and in the shampoo composition of from 2 to 30 microns.

2. A shampoo composition according to claim 1, in which the at least one surfactant is present in an amount of from 0.1 to 50% by weight of the composition.

3. A shampoo composition according to claim 1, in which the anionic surfactant is selected from the group consisting of sodium lauryl sulphate, triethanolamine lauryl sulphate, triethanolamine monolauryl phosphate, sodium lauryl ether sulphate 2EO, sodium lauryl ether sulphate 3EO, ammonium lauryl sulphate, ammonium lauryl ether sulphate 1EO, ammonium lauryl ether sulphate 2EO, ammonium lauryl ether sulphate 3EO and mixtures thereof.

4. A shampoo composition according to claim 1, in which the amphoteric surfactant is selected from the group consisting of cocamidopropylbetaine, lauryl betaine and sodium cocamphopropionate.

5. A shampoo composition according to claim 1, in which the insoluble, non volatile silicone is present in an amount of from 0.01 to 20% by weight of the composition.

6. A shampoo composition according to claim 1, in which the insoluble, non volatile silicone is selected from the group consisting of polydimethylsiloxanes.

7. A shampoo composition according to claim 1, in which the cationic hair conditioning polymer is present in an amount of 0.01 to 3% by weight of the composition.

8. A shampoo composition according to claim 1, in which the cationic hair conditioning polymer is selected from the group consisting of cationic derivatives of guar gum, cationic cellulose ether derivatives and cationic polyacrylamides.

9. A method of making the aqueous shampoo composition of claim 1, comprising mixing together water, the surfactant, the cationic conditioning polymer and a preformed aqueous emulsion of the silicone, wherein the silicone in the emulsion and in the shampoo composition has an average particle size of from 2 to 30 microns.

10. A shampoo composition according to claim 1, wherein the insoluble nonvolatile silicone is dimethicone.

11. A shampoo composition according to claim 1, wherein the insoluble nonvolatile silicone is polydiethyl siloxane.

12. A shampoo composition according to claim 1, wherein the non-volatile silicone is an emulsion of dimethicone of 60,000 cs in nonionic surfactant, wherein said non-volatile silicone is in the form of particles having a mean particle size of about 7.7 microns.

* * * * *